United States Patent [19]

Olah et al.

[11] 3,993,587

[45] Nov. 23, 1976

[54] PROCESS FOR PREPARING SUPPORTED SUPERACID CATALYSTS SUITABLE FOR ALKYLATION OF AROMATIC HYDROCARBONS

[75] Inventors: George A. Olah, Shaker Heights, Ohio; Giuseppe Messina, Alghero (Sassari), Italy

[73] Assignee: Societa Italiana Resine S.I.R. S.p.A., Milan, Italy

[22] Filed: Nov. 19, 1974

[21] Appl. No.: 525,140

[30] Foreign Application Priority Data

Nov. 28, 1973 Italy................................. 31748/73

[52] U.S. Cl............................. 252/429 R; 252/432; 252/439; 252/441; 252/442
[51] Int. Cl.²........................................... B01J 31/02
[58] Field of Search................ 252/429 R, 441, 442, 252/439, 432

[56] References Cited
UNITED STATES PATENTS

| | | | |
|---|---|---|---|
| 1,939,647 | 12/1933 | Arnold et al........................ | 252/441 |
| 2,536,841 | 1/1951 | Dornte et al....................... | 252/439 |
| 2,965,686 | 12/1960 | Prill .................................... | 252/441 |
| 3,515,679 | 6/1970 | Gacth et al. ....................... | 252/432 |
| 3,551,516 | 12/1970 | Ashley et al. .................. | 252/441 X |
| 3,746,657 | 7/1973 | Miller et al. ....................... | 252/432 |

*Primary Examiner*—Patrick P. Garvin
*Assistant Examiner*—John P. Sheehan
*Attorney, Agent, or Firm*—Sughrue, Rothwell, Mion, Zinn and Macpeak

[57] ABSTRACT

Supported superacid catalysts active in the alkylation of aromatic hydrocarbons are obtained by treating an alumina-containing support at a temperature of at least 400° C and contacting the support at a temperature of at least 150° C with a Lewis or Bronsted acid defined by one of the formulae: $MX_n$, $HMX_{n+1}$ and $MOX_m$, wherein M stands for a metal belonging to Groups IIIA, IVB, VA, VB and VIB of the Periodic System of Elements, X is a halogen (with the exception of iodine), $n$ is an integer from 3 to 6 and $m$ is an integer from 1 to 4.

17 Claims, No Drawings

PROCESS FOR PREPARING SUPPORTED SUPERACID CATALYSTS SUITABLE FOR ALKYLATION OF AROMATIC HYDROCARBONS

BACKGROUND OF THE INVENTION

1. Field of the Invention

The present invention relates to a process for preparing supported superacid catalysts active in alkylation of aromatic hydrocarbons with alkylating agents, more particularly with olefinic agents.

2. Description of the Prior Art

A catalyst currently used for alkylation reactions is aluminum trichloride. In actual practice the aromatic hydrocarbon and the alkylating agent are contacted in a reaction medium containing a fluid catalytic complex formed by aluminum trichloride, hydrocarbons and a hydrogen halide. This procedure involves many drawbacks such as loss of catalyst by solubilization phenomena in the organic reaction medium entailing expensive treatments in order to remove the dissolved catalyst from the organic medium. Moreover, serious corrosion problems arise due to the acidic properties of the catalytic complex. Similar difficulties are met with in the use of further fluid catalytic complexes, such as those of boron trifluoride and similar compounds.

U.S. Pat. No. 3,050,570 describes an alkylation process carried out in the presence of a catalyst consisting of silica-magnesium oxide having adsorbed thereon boron trifluoride. According to this Patent, the liquid alkylation medium contains dissolved boron trifluoride in a proportion of 1 to 2 grams per mole of the olefinic alkylating agent in order to maintain significant reaction rates. The drawbacks described above are thereby not avoided.

Various metal halides of the Lewis acids type or the corresponding Bronsted acids are further known as alkylation catalysts.

Thus, for instance, U.S. Pat. No. 3,708,553 describes alkylation catalysts of the $MX_n$ type, wherein M is a metal belonging to Groups IVB, V or VIB of the Periodic System of Elements, X is a halogen and n an integer from 3 to 6. These catalysts can also be prepared in a supported form, that is adsorbed on inert supports. However, their use for alkylation necessitates the presence of free catalyst in the liquid reaction medium.

No supported catalyst has been found heretofore, in which the Lewis or Bronsted acids remain permanently fixed on the support, and which is so active that it can be commercially exploited in alkylation reactions.

Consequently, known processes do not avoid the drawbacks consisting in loss of catalyst in the organic reaction phase and purification of the organic phase, and corrosion problems have not found a satisfactory solution either.

The above drawbacks are avoided by the supported superacid catalysts obtained by the process of the invention allowing the obtention of alkylates totally free of catalytic residues, which can therefore be directly conveyed to distillation without any preliminary treatment. This circumstance also solves the problems relating to corrosion effects.

SUMMARY OF THE INVENTION

Thus, the present invention provides a process for preparing a superacid supported catalyst, active in alkylation of aromatic hydrocarbons, characterized by:

treating an alumina or alumina-containing support at a temperature of at least 400° C;

contacting at a temperature of at least 150° C the thus treated support with at least one Lewis or Bronsted acid selected among those belonging to the following classes:

a. metal halides defined by the general formula $MX_n$,
b. compounds of the general formula $HMX_{n+1}$, and
c. oxyhalides defined by the general formula $MOX_m$, wherein H stands for hydrogen, O for oxygen, M for a metal selected among those belonging to Groups IIIA, IVB, VA, VB and VIB of the Periodic System of Elements, X is a halogen (with the exception of iodine), $n$ is an integer from 3 to 6 and $m$ is an integer from 1 to 4. By proceeding according to the process of the invention, a catalyst is obtained in which the Lewis acid or the Bronsted acid remains permanently fixed on the support.

The term permanently fixed should be understood to mean that there is no release of catalytic residues in the medium under inherent alkylation conditions or, at least, that the residues are present in the alkylation mixtures in quantities below those that can be analytically determined.

It is therefore believed that during preparation of the catalyst some sort of interaction occurs between the support and the Lewis or Bronsted acids.

The catalyst obtained by the process of the invention is highly active in alkylation processes of aromatic hydrocarbons by alkylating, more especially olefinic, agents, even at relatively mild temperature and pressure conditions.

The activity of the catalyst is surprising, inasmuch as the prior art teaches operating in an alkylation medium in which part at least of the Lewis or Bronsted acid is present in free form.

Useful supports for the purposes of the present invention can consist essentially of alumina or combinations of alumina with at least one further metal oxide, such as an oxide of boron, tungsten, molybdenum, thorium or chromium.

Supports consisting of pure alumina or consisting essentially of alumina containing little silica, generally less than 10% by weight, and small quantities of impurities, if any, such as iron oxide, are particularly useful.

Active earths, such as those known by the trade names FILTROL or PORACEL can be employed as support, though the last-mentioned substances are not those preferred for the purposes of the invention.

Conveniently, the support is first treated at a temperature from 400° up to 900° C, preferably around 600° C, during a period of time sufficient for removing water or at least most of the water therein contained. To this end, the support is conveniently heat-treated during a period of 30 minutes at least, and generally not exceeding 10 hours. Typically, the treatment is carried out during 3–4 hours.

The thus treated support is then contacted with at least one Lewis or Bronsted acid selected in the previously defined classes of compounds, at a temperature advantageously from 150° up to 500° C.

More particularly, among the compounds of the $MX_n$ type metal fluorides are preferred, especially fluorides of antimony, aluminum, niobium, tantalum, molybdenum, tungsten, titanium and boron, such as antimony, tantalum and niobium pentafluorides and molybdenum hexafluoride.

Metal chlorides or bromides such as aluminum trichloride and tribromide, titanium tetrachloride and antimony pentachloride can also be employed.

In an embodiment of the process for preparing the catalyst, at least one metal halide $MX_n$ in vapor form is contacted with the support, at a temperature from 150° to 500° C, preferably around 300° C, and during a period of 30 minutes at least, preferably from 2 to 4 hours.

This procedure is more particularly convenient when the metal halide employed has a boiling point within the above-mentioned range of temperature, or at least near thereto, such as antimony pentafluoride (boiling point 149.5° C) and tantalum pentafluoride (boiling point 229° C).

According to another embodiment of the process of the invention, the support is impregnated, generally at room temperature (20°–25° C), with a solution of at least one metal halide $MX_n$ in a solvent and is then heat-treated at a temperature from 150° to 500° C during a period of 30 minutes at least, generally from 2 to 6 hours. Useful solvents are hydrocarbons generally or fluorocarbons such as those of the type known under the trade name FREON. Thus, for instance, FREON 113 proved to be a useful solvent for antimony and tantalum pentafluorides.

Further useful solvents are liquid sulphur dioxide and hydrogen fluoride, and fluorosulphonic acid.

According to a further embodiment of the process of the invention, the support is impregnated with a solution of a metal halide $MX_n$ in the form of a complex, then heat-treated at a temperature from 150° to 500° C during a period of at least 30 minutes, generally from 2 to 6 hours. Suitable complexes are, for example, those formed with sulphur trioxide, such as $TaF_5.nSO_3$ and $NbF_5.nSO_3$, wherein $n$ can be from 1 to 10, or with sulphur dioxide such as $SbF_5.SO_2$. Further complexes are those formed with ethers, such as etherated boron trifluoride, or compounds of the type $ArH_2^+MX^-_{n+1}$ wherein M and X have the hereinbefore defined meaning and Ar is an aryl radical. Suitable solvents for these complexes can be of various nature such as sulphur dioxide, sulphur trioxide, FREON, ethers and others.

The catalysts can similarly be prepared starting from the above defined compounds $HMX_{n+1}$ or from metal oxyhalides of the $MOX_m$ type, such as tantalum and niobium oxyfluorides.

The alkyl aromatic hydrocarbons can be prepared by contacting an aromatic hydrocarbon and an alkylating agent with the catalyst prepared according to the invention.

More particularly, the alkylating agent can be an olefin having 2 to 20 carbon atoms in the molecule, such as ethylene, propylene, butylene, hexenes and octenes. Further useful alkylating agents are alkyl halides, alkyl phosphates and alkyl sulphates. The aromatic hydrocarbons which are subjected to alkylation are typically benzene, toluene, butylbenzene, cumene or any alkyl aromatic compounds.

During the alkylation process the temperature and pressure values depend upon the nature of the aromatic hydrocarbon and alkylating agent employed. Generally, the reaction temperature ranges from 0° to 250° C and the pressure from 20 to 100 atm. The preferred temperature and pressure values are in the ranges from 80° to 150° C and from 20 to 50 atm., respectively.

The catalyst obtained by the process of the invention is particularly useful for preparing ethylbenzene, cumene and butylbenzene.

The following experimental examples will further illustrate the invention.

EXAMPLE 1

Alumina of the A948 type distributed by Fisher Scientific Co. in powder form of 200 to 800 mesh is maintained at a temperature of 600°–650° C during 3–4 hours.

The thus treated alumina is charged to a glass reactor through which tantalum pentafluoride vapors are caused to flow during 2–3 hours at 300°–400° C, followed by cooling.

40 ml of the catalyst thus obtained are charged to a 150 ml autoclave together with 70 ml benzene. The autoclave is then filled with ethylene up to a pressure of 61 atm, this leading to an exothermic reaction with a decrease in pressure down to 41–47 atm and a rise in temperature up to 50°–60° C. Ethylene is repeatedly supplied as the reaction proceeds. The reaction product is thoroughly clear and colorless and can be directly distilled without any washing.

The conversion of benzene amounts to 28%, the composition by weight of the alkylated product being: ethylbenzene 78.5%, diethylbenzenes 21.5%.

EXAMPLE 2

Alumina according to Example 1, heat treated as described in the said Example, is impregnated with a solution of the $TaF_5.2.5\ SO_3$ complex dissolved in liquid $SO_3$. The $SO_3$ excess is first evaporated at 100 mmHg column at 70° C, then the impregnated alumina is treated at 150°–200° C in anhydrous nitrogen stream during 4 hours, followed by cooling.

The resulting catalyst is employed for alkylation in the manner described in Example 1. The conversion of benzene amounts to 37%, the alkylate comprising 65.6% by weight ethylbenzene and 34.4% by weight diethylbenzenes.

EXAMPLE 3

The catalyst is prepared as described in Example 2 with the only difference that a temperature from 250° to 350° C is maintained during the flow of nitrogen.

When the alkylation reaction is carried out with the catalyst thus prepared and under the conditions of Example 1, a very clear colorless alkylate is obtained. The alkylation reaction proceeds very swiftly, a conversion of benzene of 36% being obtained in 45 minutes with a resulting alkylate comprising 73.5% ethylbenzene and 26.5% diethylbenzenes.

The diethylbenzenes are moreover formed of 26 wt.% ortho-isomer, 38 wt.% meta-isomer and 36 wt.% para-isomer.

EXAMPLE 4

An alumina of the WO101 brand distributed by the Arshaw Company, comprising 10 wt.% $WO_3$ and in the form of granules of about 3 mm, is employed.

60 ml of this alumina are heated to 600° C during 3–4 hours in a muffle-furnace, then brought into a glass reactor, through which vapors of antimony pentafluoride are conveyed during 2 hours, then tantalum pentafluoride vapors during 1 hour, at a temperature of 300° to 400° C, followed by cooling. This severe treatment yields a partly pulverized catalyst.

30 g of the resulting catalyst are charged together with 70 ml benzene into a 150 ml autoclave. The autoclave is heated to 180°–200° C, then filled with ethylene up to 61 atm. Under such temperature and pressure conditions the ethylene is reacted at a fair speed with a fall in pressure down to 27 atm.

By using the same catalyst, several tests are carried out sequentially, the results of which are summarized in Table 1.

In the Table the composition of the alkylate is given in percentage by weight.

TABLE 1

| Test | Conversion of benzene % | Composition of the alkylate: | | |
|---|---|---|---|---|
| | | ethylbenzene % | diethylbenzene % | triethylbenzene % |
| 1 | 64.3 | 49 | 35.8 | 15.2 |
| 2 | 38.7 | 69.2 | 24.7 | 3.2 |
| 3 | 52.4 | 61.7 | 32.2 | 6.1 |
| 4 | 53.8 | 57.0 | 35.5 | 7.4 |

EXAMPLE 5

Alumina of the 1404 brand distributed by the Harshaw Company in the form of tablets of about 3 mm is employed, heated during 4 hours at 650° C, then cooled.

60g of the heat-treated alumina are impregnated at room temperature with a solution of 7 g tantalum pentafluoride in 70 ml liquid sulphur trioxide.

The excess sulphur trioxide is then evaporated at 70° C and subatmospheric pressure, then the impregnated alumina is charged to a glass reactor at 250°–300° C, in which anhydrous nitrogen is caused to flow during 3–4 hours till no more sulphur trioxide vapors evolve, followed by cooling.

The resulting catalyst is charged into a 300 ml stainless steel autoclave provided with a thermocouple and a magnetic stirrer. The autoclave is charged with 150 ml benzene and heated to the desired temperature, whereupon ethylene is charged up to 61 atm. A very swift reaction takes place, the pressure sinking down to 13–27 atm. Ethylene is repeatedly charged. The reaction product is very clear and colorless after decanting the suspended pulverized catalyst.

This reaction product can be directly distilled without any purification.

The results of the tests carried out at various temperatures are summarized in Table 2 in which the alkylate composition is given in percentage by weight.

EXAMPLE 6

Alumina of the 1404 brand having an $Al_2O_3$ content of 96 wt.% distributed by the Harshaw Company is employed in the form of tablets of about 3 mm.

This alumina is heated at 600° C during 3–4 hours, then cooled and impregnated with 9 g tantalum pentafluoride in a liquid sulphur trioxide solution.

The excess sulphur trioxide is evaporated at 70° C and subatmospheric pressure, then the impregnated alumina is charged to a glass reactor and heated during 2–3 hours at 250°–350° C while anhydrous nitrogen is caused to flow therethrough, followed by cooling.

50g of the resulting catalyst are charged to a stainless steel autoclave provided with a thermocouple and a magnetic stirrer. 150 ml benzene are also charged to the autoclave.

While the mass is stirred, it is heated to 200° C and ethylene is charged at this temperature up to 47–48 atm. A swift reaction takes place (pressure sinks in 60 seconds by 20–21 atm) and the pressure is allowed to sink down to 20–27 atm.

Ethylene is repeatedly charged till a conversion of 58% calculated on benzene is reached.

The alkylate has the following composition by weight: 59% ethylbenzene, 27% diethylbenzenes, 8% triethylbenzenes, other components 7%.

Table 2

| Test | Temperature | Conversion benzene % | Composition of the alkylate: | | | |
|---|---|---|---|---|---|---|
| | | | % ethyl-benzenes | % diethyl benzenes | % triethyl benzenes | % others components |
| 1 | 70–80 | 45 | 57.63 | 30.18 | 8.18 | 4 |
| 2 | 40–30 | 61.2 | 61.68 | 25.46 | 8.39 | 4.46 |
| 3 | 130 | 50.0 | 61.72 | 26.45 | 7.62 | 4.21 |

We claim:
1. A method of preparing a superacid supported catalyst, active in the alkylation of aromatic hydrocarbons, comprising the steps of (1) heat-treating a support consisting essentially of alumina at a temperature of at least 400° C, and (2) contacting the thus treated support with at least one Lewis or Bronsted acid selected from the following classes:
 a. metal halides defined by the general formula $MX_n$,
 b. compounds of the general formula $HMX_{n+1}$, and
 c. oxyhalides defined by the general formula $MOX_m$, wherein H stands for hydrogen, O for oxygen, M for a metal selected in the Groups IIIA, IVB, VA, VB and VIB of the Periodic System of Elements, X for a halogen other than iodine, n is an integer from 3 to 6 and m is an integer from 1 to 4, and heat-treating at a temperature of at least 150° C during said contact.
2. The method of claim 1, wherein said support consists of alumina.
3. The method of claim 1, wherein said support consists essentially of at least 90% by weight alumina and less than 10 wt.% silica.
4. The method of claim 1, wherein said support consists essentially of alumina combined with at least one oxide chosen from the group consisting of boron, tungsten, molybdenium, thorium and chromium oxides.
5. The method of claim 1, wherein said support during step (1) is heat-treated at a temperature from 400° to 900° C for a period from 30 minutes to 10 hours.
6. The method of claim 1, wherein said support during step (1) is heat-treated at a temperature of about 600° C for a period from 3 to 4 hours.

7. The method of claim 1, wherein said temperature maintained during step (2) is from 150° to 500° C.

8. The method of claim 1, wherein said metal halides are metal fluorides.

9. The method of claim 8, wherein said metal fluorides are chosen from the group consisting of antimony, aluminium, niobium, tantalum, molybdenum, tungsten, titanium and boron fluorides.

10. The method of claim 1, wherein during step (2) at least one metal halide $MX_n$ in vapor form is contacted with said support at a temperature from 150° to 500° C for a period of at least 30 minutes.

11. The method of claim 10, wherein said support is contacted with at least one metal halide $MX_n$ in vapor form at a temperature of about 300° C during a period from 2 to 4 hours.

12. The method of claim 1, wherein step (2) comprises first impregnating the heat-treated support with at least one metal halide $MX_n$ dissolved in a solvent chosen from the group consisting of hydrocarbons, fluorocarbons, sulphur dioxide, hydrogen fluoride and fluorosulphonic acid, and then the impregnated support is heat-treated at a temperature from 150° to 500° C for a period of at least 30 minutes.

13. The method of claim 12, wherein in step (2) the impregnated support is heat-treated for a period from 2 to 6 hours.

14. The method of claim 1, wherein step (2) comprises first impregnating the heat-treated support with a solution of said metal halide in the form of a complex chosen from the group consisting of the complexes of metal halides $MX_n$ with sulphur dioxide, sulphur trioxide and ethers and $ArH_2^+ MX^-_{n+1}$ complexes, Ar being an aryl radical, and then the impregnated support is heat-treated at a temperature from 150° to 500° C for a period of at least 30 minutes.

15. The method of claim 14, wherein in step (2) the impregnated support is heat-treated for a period from 2 to 6 hours.

16. The method of claim 1, wherein the said oxyhalides are chosen from the group of tantalum and niobium oxyfluorides.

17. The method of claim 12, wherein in step (2) said impregnating of said heat-treated support is conducted at a temperature of about 20°—25 C.

* * * * *